US010922961B2

(12) United States Patent
Peesapati et al.

(10) Patent No.: US 10,922,961 B2
(45) Date of Patent: Feb. 16, 2021

(54) REMOTE COMMUNICATION WITH MULTIPLE DIALYSIS MACHINES

(71) Applicant: Fresenius Medical Care Holdings, Inc., Waltham, MA (US)

(72) Inventors: Sameera Anirudh Peesapati, Pittsburg, CA (US); David Yuds, Hudson, NH (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/351,623

(22) Filed: Mar. 13, 2019

(65) Prior Publication Data
US 2020/0294392 A1 Sep. 17, 2020

(51) Int. Cl.
*G08C 23/02* (2006.01)
*A61M 1/14* (2006.01)

(52) U.S. Cl.
CPC .............. *G08C 23/02* (2013.01); *A61M 1/14* (2013.01); *A61M 2205/3379* (2013.01); *A61M 2205/3576* (2013.01)

(58) Field of Classification Search
CPC ......... E05B 81/76; E05B 81/77; B60R 25/31; A61M 1/14; G08C 23/02
See application file for complete search history.

(56) References Cited

U.S. PATENT DOCUMENTS

| 4,034,300 A | 7/1977 | Streckenbach |
| 5,230,341 A | 7/1993 | Polaschegg |
| 6,068,612 A | 5/2000 | Bowman et al. |
| 6,212,936 B1 | 4/2001 | Meisberger |
| 7,278,983 B2 * | 10/2007 | Ireland ................... G16H 20/17 604/66 |

(Continued)

FOREIGN PATENT DOCUMENTS

| DE | 19840965 | 3/2000 |
| WO | WO 2013/168170 | 11/2013 |

OTHER PUBLICATIONS

Getreuer et al. "Ultrasonic Communication Using Consumer Hardware", Jun. 2018, IEEE Transactions on Multimedia, pp. 1277-1278 (Year: 2018).*

(Continued)

*Primary Examiner* — Daniell L Negron
(74) *Attorney, Agent, or Firm* — Fish & Richardson P.C.

(57) ABSTRACT

A remote control device may be used to wirelessly control functions of one or more dialysis machines, e.g. in a clinic environment and without requiring direct contact with the dialysis machines. Components of the remote control device may include control interfaces, e.g. buttons, for controlling and adjusting functions of a medical device, such as a dialysis machine, including, for example, volume control, blood pump control blood flow rate control and/or adjusting the level in the venous drip chamber, among other control features. Display of the remote control device may include one or more screens that may display information of one or more dialysis machines, patients undergoing dialysis treatment, and/or alarms or alerts of one or more of the dialysis machines. In an implementation, ultrasonic communication is used to wirelessly exchange information and commands between the remote control device and the one or more dialysis machines.

20 Claims, 5 Drawing Sheets

(56) References Cited

U.S. PATENT DOCUMENTS

| | | |
|---|---|---|
| 7,661,293 B2 | 2/2010 | Dam |
| 7,661,294 B2 | 2/2010 | Dam |
| 7,694,565 B2 | 4/2010 | Koerdt et al. |
| 8,836,519 B2 | 9/2014 | Wright et al. |
| 9,250,216 B2 | 2/2016 | Wright et al. |
| 9,585,995 B2 | 3/2017 | Wright et al. |
| 9,662,438 B2 * | 5/2017 | Kamen ............ A61M 5/14244 |
| 9,800,663 B2 | 10/2017 | Arrizza |
| 10,086,125 B2 | 10/2018 | Wright et al. |
| 2005/0085760 A1 | 4/2005 | Ware et al. |
| 2013/0018355 A1 | 1/2013 | Brand et al. |
| 2018/0001010 A1 | 1/2018 | Blümler et al. |
| 2018/0027077 A1 * | 1/2018 | Melodia ............... A61B 5/0022 370/254 |
| 2018/0036469 A1 * | 2/2018 | Crnkovich ............ A61M 1/267 |
| 2018/0316505 A1 | 11/2018 | Cohen et al. |

OTHER PUBLICATIONS

Zhou et al., "Graphene electrostatic microphone and ultrasonic radio," Proceedings of the National Academy of Sciences 112(29):8942-8946, Jul. 2015.

International Search Report and Written Opinion in Application No. PCT/US2020/020928, dated Jun. 5, 2020, 15 pages.

\* cited by examiner

REMOTE COMMUNICATION WITH MULTIPLE DIALYSIS MACHINES

TECHNICAL FIELD

This application relates generally to systems and methods for remote communication with multiple medical devices, in particular, dialysis machines.

BACKGROUND

Medical devices, such as dialysis machines, are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. Before the blood is returned to the body, air bubbles are removed from the blood to inhibit embolisms. The process of removing air is typically accomplished through use of a venous drip chamber, which is located downstream of the blood outlet of a dialyzer and upstream of the venous blood return of the patient.

During peritoneal dialysis, the patient's peritoneal cavity is periodically infused with dialysate, or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance. Both HD and PD machines may include displays with touch screens or other user interfaces that display information of a dialysis treatment and/or enable an operator or patient to interact with the machine.

Dialysis machine functions, like raising the blood level in the venous drip chamber, may be accessed via a touch screen and involve physical contact with the machines. When there is more than one dialysis machine in an environment, the clinician must change gloves every time a machine is to be accessed in order to prevent cross-contamination between machines and patients. More generally, because of the risk of cross contamination between patients and machines, there is a need to be able to handle the operation of multiple components, such as blood pump, venous alarms, and bolus, on multiple machines in a safe and efficient manner.

Accordingly, it would be desirable to provide a system that addresses the above-noted concerns and other issues.

SUMMARY

According to the system described herein, a medical system includes a first medical device, a second medical device, and a remote control device. The remote control device is communicatively coupled to the first medical device and the second medical device, in which the remote control device is wirelessly paired and coupled to the first medical device via a first communication channel and is wirelessly paired and coupled to the second medical device via a second communication channel. The first medical device and the second medical device are independently controllable by the remote control device. One or more of the first medical device and the second medical device may be a dialysis machine. One or more of the first communication channel and the second communication channel may be an ultrasonic communication channel, and the remote control device may include an ultrasonic communication component. The remote control device may include an interface that enables selection and control of the first medical device independently from selection and control of the second medical device. The remote control device may include an adjustment for a level of a venous drip chamber.

According further to the system described herein, a method is provided for remotely controlling multiple medical devices. A first medical device is wirelessly paired and coupled to a remote control device over a first communication channel. A second medical device is wirelessly paired and coupled to the remote control device over a second communication channel. The method includes independently controlling the first medical device and the second medical device using the remote control device. One or more of the first medical device and the second medical device may be a dialysis machine. One or more of the first communication channel and the second communication channel may be an ultrasonic communication channel. Independently controlling the first medical device and the second medical device using the remote control device may include separately selecting representations of the first medical device and the second medical device on an interface of the remote control device. A level of a venous drip chamber of each of the first medical device and the second medical device may be independently adjusted.

According further to the system described herein, an ultrasonic remote control device for a medical device includes an ultrasonic transmission component, an ultrasonic receiving component, and at least one processor. The at least one processor enables independent pairing and communication between the ultrasonic remote control device and a first medical device over a first ultrasonic communication channel using the ultrasonic transmission component and the ultrasonic receiving component and between the ultrasonic remote control device and a second medical device over a second ultrasonic communication channel using the ultrasonic transmission component and the ultrasonic receiving component. One or more of the first medical device and the second medical device may be a dialysis machine. The ultrasonic remote control device may further include an interface that enables independent selection and control of the first medical device and the second medical device.

BRIEF DESCRIPTION OF THE DRAWINGS

Embodiments and features of the system described herein are explained with reference to the several figures of the drawings, which are briefly described as follows.

DETAILED DESCRIPTION

Figure 1:
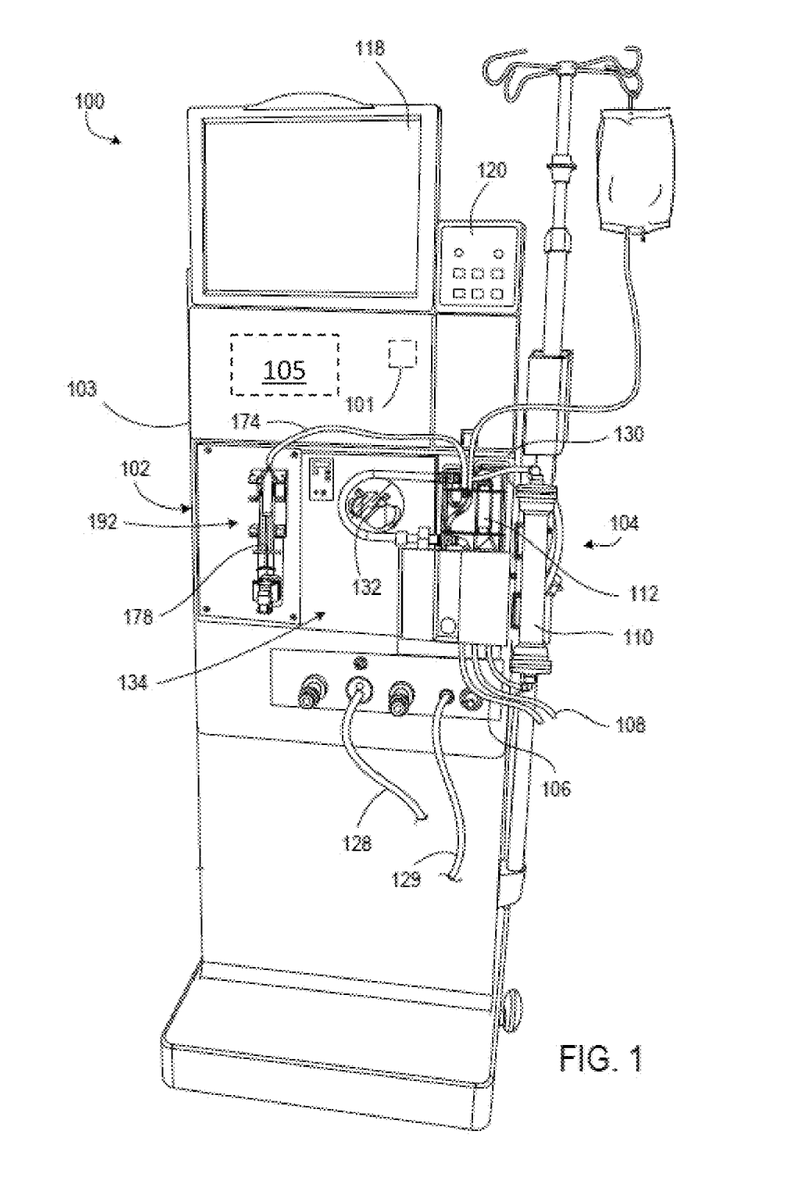
FIG. 1 illustrates an exemplary embodiment of a dialysis machine, specifically a hemodialysis machine, configured in accordance with the present disclosure.

FIG. 1 shows a hemodialysis system 100. The hemodialysis system 100 includes a hemodialysis machine 102 connected to a disposable blood component set 104 that partially forms a blood circuit. During hemodialysis treatment, an operator connects arterial and venous patient lines 106, 108 of the blood component set 104 to a patient. The blood component set 104 may include an air management device 112 that may include, for example, a venous drip chamber.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment that is sized and shaped to receive the blood component set 104.

The blood pump 132 is part of a blood pump module 134. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in a drip chamber.

The hemodialysis machine 102 further includes a dialysate circuit formed by the dialyzer 110, various other dialysate components, and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

A drain line 128 and an ultrafiltration line 129 extend from the hemodialysis machine 102. The drain line 128 and the ultrafiltration line 129 are fluidly connected to the various dialysate components and dialysate lines inside the housing 103 of the hemodialysis machine 102 that form part of the dialysate circuit. During hemodialysis, the dialysate supply line carries fresh dialysate to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 128. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a user interface with input devices such as a touch screen 118 and a control panel 120. The touch screen 118 and the control panel 120 allow the operator to input various different treatment parameters to the hemodialysis machine 102 and to otherwise control the hemodialysis machine 102. The touch screen 118 displays information to the operator of the hemodialysis system 100.

The hemodialysis machine 102 also includes a control unit 101 (e.g., a processor) configured to receive signals from and transmit signals to the touch screen 118 and the control panel 120. The control unit 101 can control the operating parameters of the hemodialysis machine 102, for example, based at least in part on the signals received by the touch screen 118 and the control panel 120. The hemodialysis machine 102 may also include a communication unit 105 that may be provided for wireless communication with a remote control device, as further described in detail elsewhere herein, and may be communicatively coupled with the control unit 101.

Although discussed herein principally in connection with a particular configuration of hemodialysis machine, the system described herein may be used and implemented in connection with other configurations or types of hemodialysis machines as well as other medical devices, including peritoneal dialysis machines, that would benefit from remote communication and control.

Figure 2:
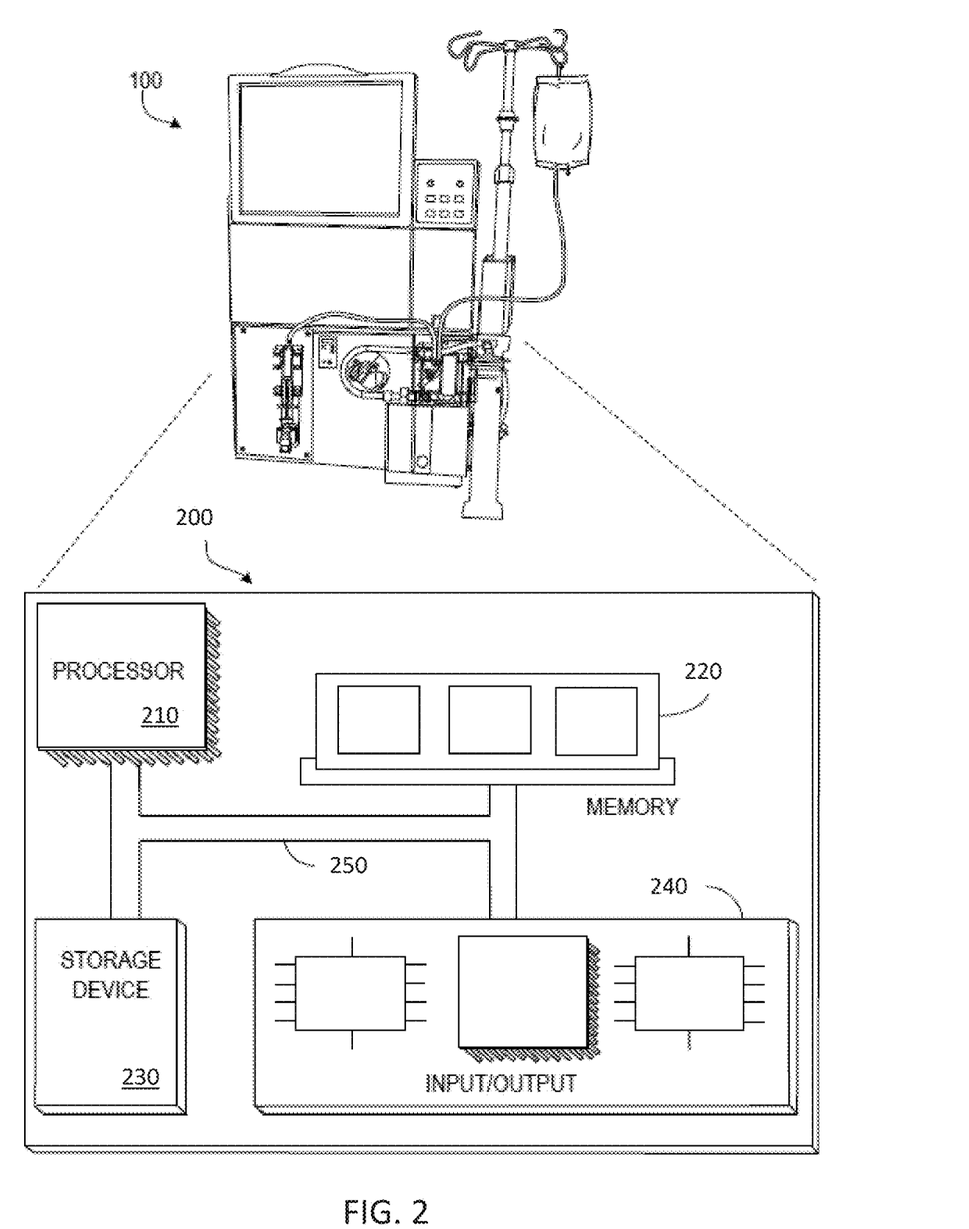
FIG. 2 is a block diagram of an example computer system illustrated in connection with the dialysis machine.

FIG. 2 is a block diagram of an example computer system 200 illustrated in connection with the dialysis machine 100. For example, the control unit 101 discussed above could be an example of the system 200 described here. The system 200 includes a processor 210, a memory 220, a storage device 230, and an input/output device 240. Each of the components 210, 220, 230, and 240 can be interconnected, for example, using a system bus 250. The processor 210 is capable of processing instructions for execution within the system 200. The processor 210 can be a single-threaded processor, a multi-threaded processor, and/or other computer. The processor 210 is capable of processing instructions stored in the memory 220 or on the storage device 230. The memory 220 stores information within the system 200. In some implementations, the memory 220 is a computer-readable medium. The memory 220 can, for example, be a volatile memory unit or a non-volatile memory unit.

The storage device 230 is capable of providing mass storage for the system 200. In some implementations, the storage device 230 is a non-transitory computer-readable medium. The storage device 230 can include, for example, a hard disk device, an optical disk device, a solid-state drive, a flash drive, magnetic tape, or some other large capacity storage device. The storage device 230 may alternatively be a cloud storage device, e.g., a logical storage device including multiple physical storage devices distributed on a network and accessed using a network. In some implementations, the information stored on the memory 220 can also or instead be stored on the storage device 230.

The input/output device 240 provides input/output operations for the system 200. In some implementations, the input/output device 240 includes one or more of network interface devices (e.g., an Ethernet card), a serial communication device (e.g., an RS-232 10 port), and/or a wireless interface device (e.g., a short-range wireless communication device, an 802.11 card, a wireless modem (3G, 4G, 5G)). In some implementations, the input/output device 240 includes driver devices configured to receive input data and send output data to other input/output devices, e.g., a keyboard, a printer, and display devices (such as the touch screen display 118). In some implementations, mobile computing devices, mobile communication devices, and other devices are used. The input/output device 240 may further include the communication component 105 that is discussed in more detail elsewhere herein.

In some implementations, the system 200 is a microcontroller. A microcontroller is a device that contains multiple elements of a computer system in a single electronics package. For example, the single electronics package could contain the processor 210, the memory 220, the storage device 230, and input/output devices 240.

Figure 3:
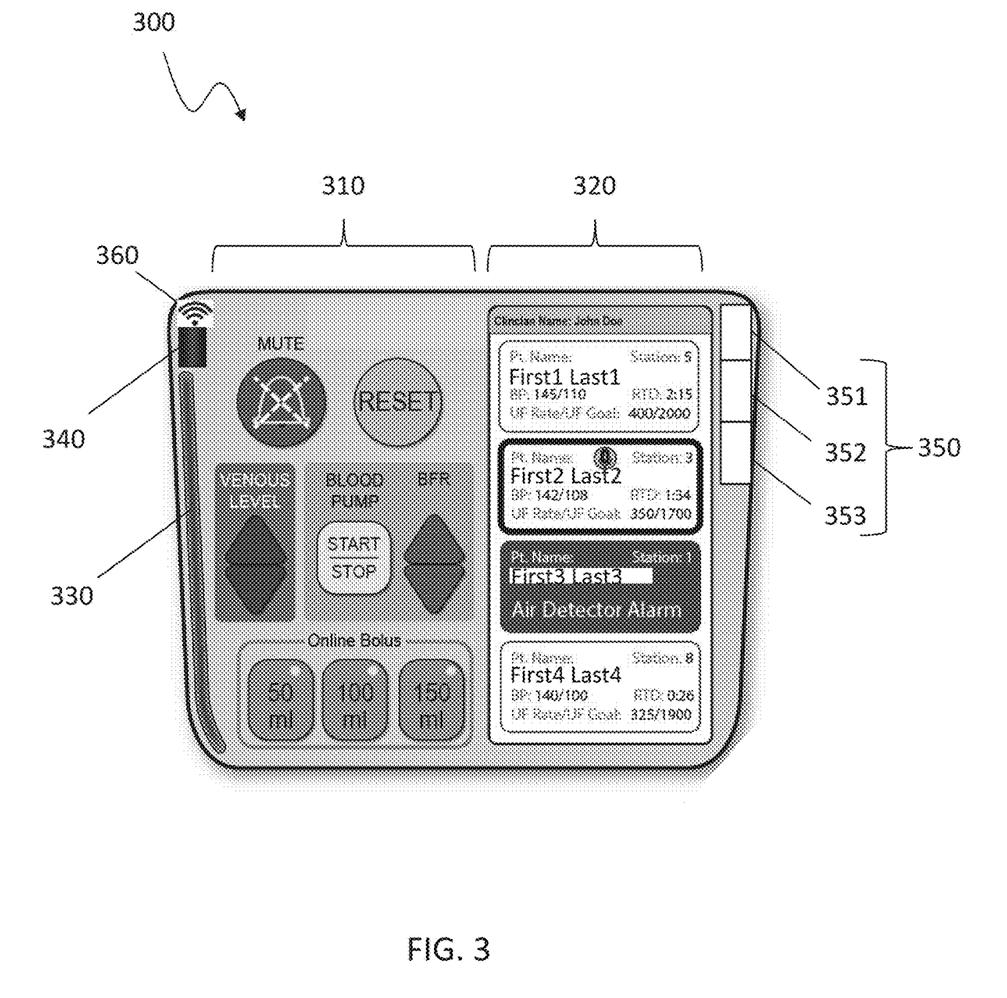
FIG. 3 is a schematic illustration of an embodiment of a remote control device that may be used in connection with the system described herein.

FIG. 3 is a schematic illustration of an embodiment of a remote control device 300 that may be used in connection with the system described herein. The remote control device 300 may be used to wirelessly control functions of one or more dialysis machines, e.g. in a clinic environment and without requiring direct contact with the dialysis machines. In an embodiment, the remote control device 300 may be referred to as a "Hemote." Components 310 of the remote control device 300 may include control interfaces, e.g. buttons, for controlling and adjusting functions of a medical device, such as a dialysis machine, including, for example, volume control, blood pump control blood flow rate control and/or adjusting the level in the venous drip chamber, among other control features. Components 310 may also include control interfaces providing the ability to deliver saline/replacement fluid boluses at the dialysis machine. Display 320 of the remote control device 300 may include one or more screens that may display information of one or more dialysis machines, patients undergoing dialysis treatment, and/or alarms or alerts of one or more of the dialysis machines. The remote control device 300 may also include suitable processors for performing the described functions and may include a battery as a power source.

The remote control device 300 may be stored remotely from the dialysis machines and/or may be affixed to the side of one or more dialysis machines, for example using a magnetic attachment, and it may be stored in a location where it can wirelessly charge its battery when not in use. A user feedback component 330, such as a rocker-type switch with tactile feedback, may ensure confident operation of the controls without needing to check hand-placement. In an embodiment, the user feedback component may also include biometric authentication components, such as a fingerprint authentication that ensures that once a user is authenticated, only patients assigned to them will appear on the screen 320. Other authentication mechanisms may also be used, such as inclusion of a camera and processing to enable face recognition capability. Additionally, visual and audible alert interface components (e.g. lights and/or speakers) 340 could be incorporated to facilitate easier verification of controlled functions, e.g., an appropriate venous drip chamber level.

In an implementation, the remote control device 300 may include an ultrasonic communication component 350 that provides for wireless communication in the form of ultrasonic wireless communication. The ultrasonic communication component 350 may include an ultrasonic transmitting component 351 from which an ultrasonic signal may be emitted that may be used to enable selecting and pairing to a particular dialysis machine in a clinic environment. The ultrasonic communication component 350 may also include an ultrasonic receiving component 352 that may detect and receive an ultrasonic signal from one or more dialysis machines, as further described elsewhere herein. The ultrasonic communication component 350 may also include one or more processors and/or other processing components 353 for providing signal processing capabilities, for example, ultrasonic signal processing functions. By way of example, for a discussion of concepts and components of an ultrasonic communication system, reference is made to Zhou et al., "Graphene electrostatic microphone and ultrasonic radio," PNAS Jul. 21, 2015 112 (29) 8942-8946, which is incorporated herein by reference.

The user may select representations of the patients and/or stations on the display 320 of the remote control device 300. For example, the display 320 may include one or more screens showing patient tabloid information, such as patient name, station, last blood pressure, remaining time of dialysis, ultrafiltration (UF) rate/UF goal, Kt/V etc. In an embodiment, the user can only work on one machine at a time; the station selected on the display 320 may be indicated by a thick frame around the patient tabloid. During an alarm, the screen may highlight the patient tabloid and populate the alarm with alarm details. The remote control device 300 may also vibrate and/or otherwise activate the user feedback component 330 and/or the alert interface components 340 to alert the user. When there are multiple alarms, the screen 320 may display the alarms in an order based on severity and/or based on an order of time concerning the earliest alarm, for example.

In various implementations, more functions may be included, such as linking to a medical information system. For example, when a patient treatment is finished, the data may be automatically sent to a medical information system and/or over a connected health network, using a wireless communication component 360 that may be different from the ultrasonic communication component 350, such as by using Wi-Fi, Bluetooth and/or other local area network wireless connection technology. More clinical workflow steps and automation intelligence may be built into the technology, including patient identification and communicating with peripheral medical devices, such as a blood pressure cuffs, weight scales etc. The system described herein may also be used in connection with distributing alerts to a remote location and/or to a patient using the medical device, such as to the patient's smartphone, over a connected health network, for example, in the event an alert on a dialysis machine that appears on the remote control device 300 is not addressed in a specified time period. By way of example, for a description of a system for securely distributing information, including medical prescriptions, within a connected health network, reference is made to US Pub. No. 2018/0316505 A1 to Cohen et al., which is incorporated herein by reference.

Figure 4:
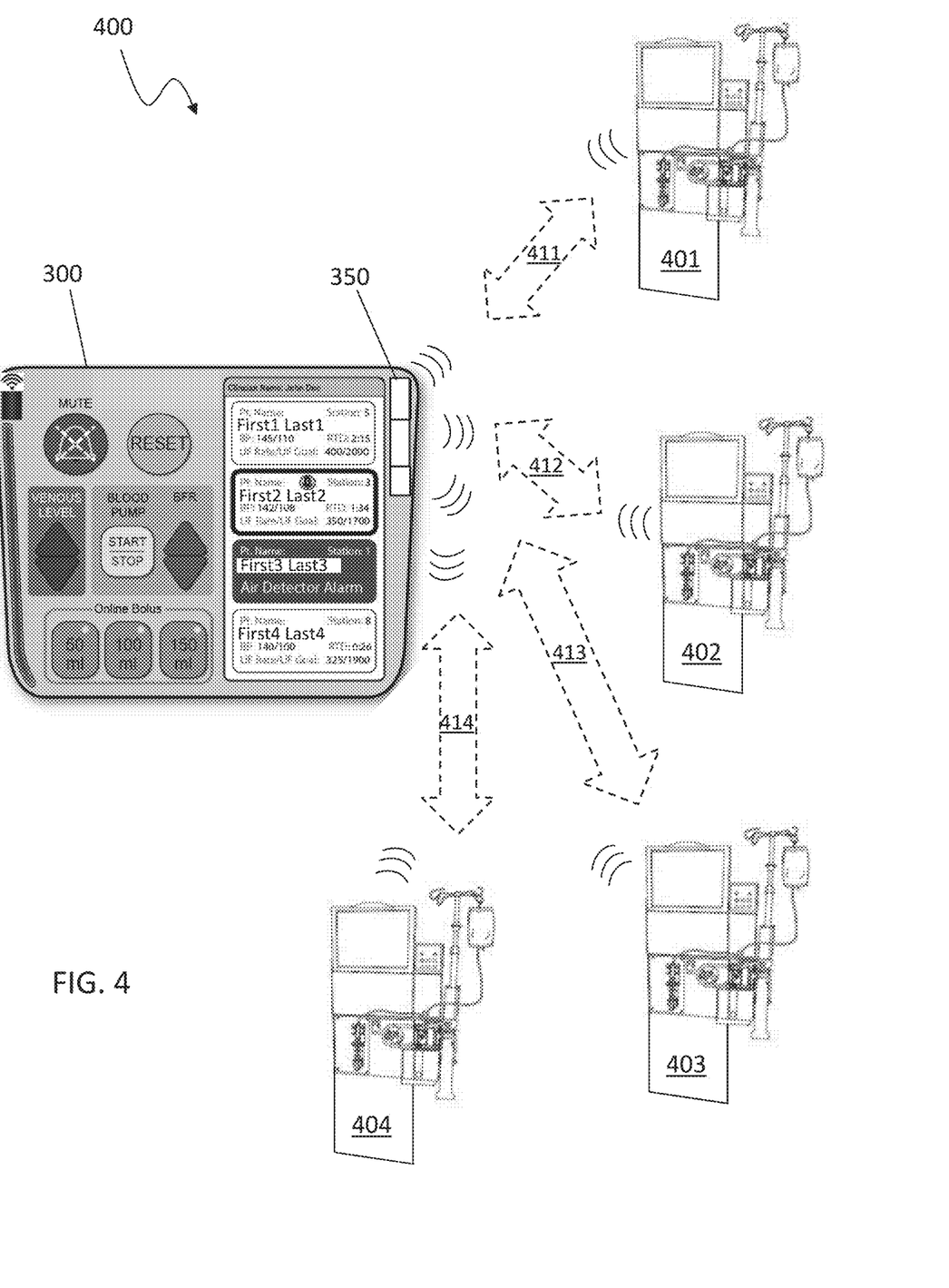
FIG. 4 is a schematic illustration of a clinic environment communication system enabling remote communication of the remote control device with multiple dialysis machines.

FIG. 4 is a schematic illustration of a clinic environment communication system 400 enabling remote communication of the remote control device 300 with multiple dialysis machines 401-404. Although four dialysis machines 401-404 are illustrated, the system described herein may be used in connection with any appropriate number of machines (e.g. 2 or more), which may depend, for example, on clinic requirements and/or appropriate patient to clinician ratios, etc. In the clinic environment, each dialysis machine may broadcast its own unique ultrasonic signal, such as an ultrasonic pulse or tone, and being a symphony unheard by human ears, that could be detected by the ultrasonic communication component 350 of the remote control device 300. In this way, the remote control device 400 may be individually and independently paired with each of the dialysis machines 401-404, illustrated by arrows 411-414 representing paired bi-directional communication channels between each of the dialysis machines 401-404 and the remote control device 300. It is noted that the ultrasonic communication channels 411-414 may be appropriately secure and the data, information and/or commands transmitted thereon may be appropriately encrypted. When the remote control device 300 is in 'listen' mode, the ultrasonic communication component 350 may be configured to identify the closest dialysis machine or sort competing tones to display multiple machine identification numbers on a selection screen of the display 320. This sorting may be used with other communications mechanisms such as Wi-Fi, Bluetooth, near field communication (NFC), optical, infrared, etc.

When the operator desires to communicate with a particular dialysis machine, he/she may select it from the list of recognized dialysis machines, such as on the display 320, and the remote control device 300 could then broadcast its own ultrasonic signal to announce the intent to link. In an embodiment, this signal may be identical to the desired dialysis machine's own ultrasonic signal followed by a secret code for that particular machine, for example. The desired dialysis machine would then broadcast an ultrasonic signal to acknowledge the established link, for example, the communication component (e.g. communication component 105) of the desired dialysis machine. The communication component of the dialysis machine can continue to send bursts of information along a unique variance pattern protocol to make the connection secure (e.g. the protocol inserts a sequence of secret "handshakes" ultrasonic pulses based on the time of day the message is being transmitted or the ultrasonic pulses are synchronized to an encrypted pattern unique to that dialysis machine.

By providing the remote control device 300 with wireless communication and pairing capability, the same device may be used to independently control multiple machines within a clinic by selection and control using the interface 320 of the remote control device 300. For example, the remote control device 300 may be used to raise the level of the venous drip chamber on multiple machines within a clinic, made possible by direct control of only the machine at which the remote is directed and/or paired. This would then allow a clinician to carry one remote and respond to many alarms on any machine without the need to make physical contact with the machine, thereby improving infection control from cross-contamination.

Figure 5:
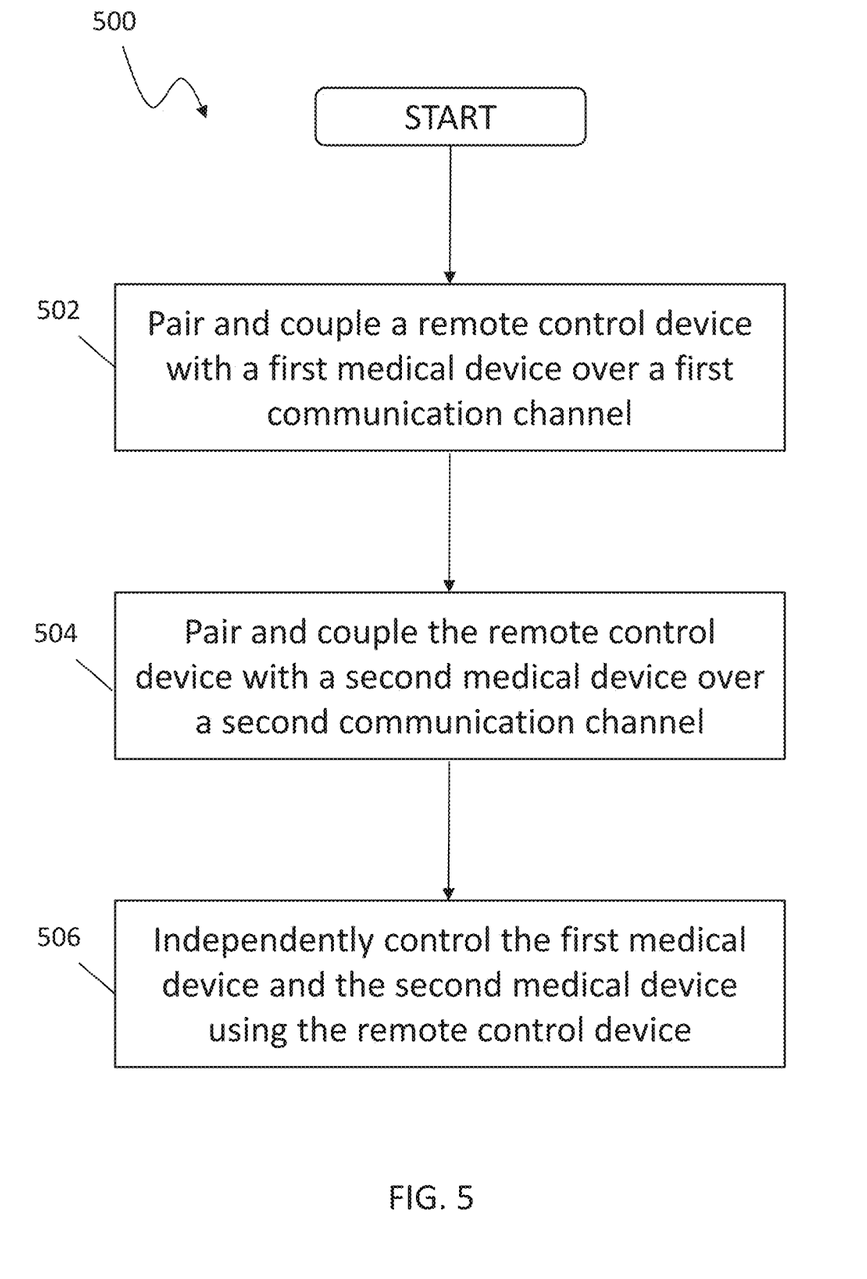
FIG. 5 is a flow diagram showing a process for remotely controlling multiple medical devices, such as multiple dialysis machines in a clinic environment.

FIG. 5 is a flow diagram 500 showing processing for remotely controlling multiple medical devices, such as multiple dialysis machines in a clinic environment. At a step 502, a remote control device is paired and coupled with a first medical device over a first communication channel. In an embodiment, the first communication channel is an ultrasonic communication channel. After the step 502, at a step 504, the remote control device is paired and coupled with a second medical device over a second communication channel. In an embodiment, the second communication channel is an ultrasonic communication channel. After the step 504, at a step 506, a user of the remote control device may select and independently control the first medical device and/or the second medical device. For example, the user may select a representation (e.g., corresponding image and/or text) of the first medical device using an interface of the remote control device and may adjust a level of the venous drip chamber of the first medical device. Then, the user may select a representation of the second medical device using the interface of the remote control device and may adjust a level of the venous drip chamber of the second medical device, independently of the first medical device. The control of both the first medical device and the second medical device is done wirelessly and without the user having to physically contact either the first medical device or the second medical device. The processing described herein may be further performed and repeated with any appropriate number of medical devices in a clinic environment.

Implementations discussed herein may be combined with each other in appropriate combinations in connection with the system described herein. Additionally, in some instances, the order of steps in the flow diagrams, flowcharts and/or described flow processing may be modified, where appropriate. The system may further include a display and/or other computer components for providing a suitable interface with a user and/or with other computers. Aspects of the system described herein may be implemented or controlled using software, hardware, a combination of software and hardware and/or other computer-implemented or computer-controlled modules or devices having described features and performing described functions. Data exchange and/or signal transmissions to, from and between components of the system may be performed using wired or wireless communication. This communication may include use of one or more transmitter or receiver components that securely exchange information via a network, such as the Internet, and may include use of components of local area networks (LANs) or other smaller scale networks, such as Wi-Fi, Bluetooth or other short range transmission protocols, and/or components of wide area networks (WANs) or other larger scale networks, such as mobile telecommunication networks.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media, a memory card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system. The meanings of any method steps of the invention(s) described herein are intended to include any suitable method of causing one or more parties or entities to perform the steps unless a different meaning is expressly provided or otherwise clear from the context.

As used herein, an element or operation recited in the singular and preceded with the word "a" or "an" should be understood as not excluding plural elements or operations, unless such exclusion is explicitly recited. References to "one" embodiment or implementation of the present disclosure are not intended to be interpreted as excluding the existence of additional embodiments that also incorporate the recited features. Furthermore, a description or recitation in the general form of "at least one of [a], [b] or [c]," or similar, should be generally construed to include [a] alone, [b] alone, [c] alone, or any combination of [a], [b] and [c].

Embodiments and implementations of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A medical system, comprising:
a first medical device;
a second medical device; and
a remote control device communicatively coupled to the first medical device and the second medical device, wherein the remote control device is wirelessly paired via a first linking ultrasonic signal and coupled to communicate via a first communication ultrasonic signal to the first medical device via a first ultrasonic communication channel and wirelessly paired via a second linking ultrasonic signal and coupled to communicate via a second communication ultrasonic signal to the second medical device via a second ultrasonic communication channel, and wherein the first medical device and the second medical device are independently controllable by the remote control device, wherein the remote control device includes an ultrasonic communication component and an interface that displays, at a same time, representations of both the first medical device and the second medical device and enables selection and control of the first medical device independently from selection and control of the second medical device, and wherein the remote control device controls only one of the first medical device or the second medical device at a time using the ultrasonic communication component.

2. The medical system of claim 1, wherein one or more of the first medical device and the second medical device is a dialysis machine.

3. The medical system of claim 1, wherein the remote control device includes an adjustment interface for adjusting a level of a venous drip chamber of the first medical device using the first ultrasonic communication channel or for adjusting a level of a venous drip chamber of the second medical device using the second ultrasonic communication channel.

4. The medical system of claim 1, wherein the remote control device broadcasts the first linking ultrasonic signal or the second linking ultrasonic signal to announce an intent to establish a communication link to a selected one of the first medical device or the second medical device, and wherein the selected one of the first medical device or the second medical device broadcasts an acknowledgement ultrasonic signal to acknowledge the communication link established with the remote control device.

5. The medical system of claim 4, wherein, after acknowledging the communication link, the selected one of the first medical device or the second medical device sends information bursts along a pattern protocol to make the communication link secure.

6. The medical system of claim 5, wherein the information bursts include one or more of a sequence of ultrasonic pulses that is based on a time of day transmission or ultrasonic pulses that are synchronized to a pattern unique to the selected one of the first medical device or the second medical device.

7. The medical system of claim 1, wherein the remote control device further comprises a wireless communication component that is different from the ultrasonic communication component, and wherein the remote control device is wirelessly coupled to a network and adapted to distribute information received from one or more of the medical devices to a remote location.

8. A method for remotely controlling multiple medical devices, comprising:
wirelessly pairing and coupling a first medical device to a remote control device over a first ultrasonic communication channel, the first medical device being paired via a first linking ultrasonic signal and coupled to communicate via a first communication ultrasonic signal with the remote control device;
wirelessly pairing, via a second linking ultrasonic signal and coupling to communicate via a second communication link, a second medical device to the remote control device over a second ultrasonic communication channel; and
independently controlling the first medical device and the second medical device using the remote control device, wherein the remote control device includes an ultrasonic communication component and an interface that displays, at a same time, representations of both the first medical device and the second medical device and enables selection and control of the first medical device independently from selection and control of the second medical device, and wherein the remote control device controls only one of the first medical device or the second medical device at a time using the ultrasonic communication component.

9. The method of claim 8, wherein one or more of the first medical device and the second medical device is a dialysis machine.

10. The method of claim 8, wherein a level of a venous drip chamber of the first medical device is adjusted using the remote control device and is adjusted independently of a level a venous drip chamber of the second medical device.

11. The method of claim 8, wherein the remote control device broadcasts the first or the second linking ultrasonic signal to announce an intent to establish the first or the second communication link to a selected one of the first medical device or the second medical device, and wherein the selected one of the first medical device or the second medical device broadcasts an acknowledgement ultrasonic signal to acknowledge the communication link established with the remote control device.

12. The method of claim 11, wherein, after acknowledging the communication link, the selected one of the first medical device or the second medical device sends information bursts along a pattern protocol to make the communication link secure.

13. The method of claim 12, wherein the information bursts include one or more of a sequence of ultrasonic pulses that is based on a time of day of transmission or ultrasonic pulses that are synchronized to a pattern unique to the selected one of the first medical device or the second medical device.

14. The method of claim 8, wherein the remote control device further comprises a wireless communication component that is different from the ultrasonic communication component, and wherein the remote control device is wirelessly coupled to a network and adapted to distribute information received from one or more of the medical devices to a remote location.

15. An ultrasonic remote control device for a medical device, comprising:
   an ultrasonic transmission component;
   an ultrasonic receiving component;
   at least one processor that enables independent pairing via a first linking ultrasonic signal and coupling to communicate via a first communication ultrasonic signal between the ultrasonic remote control device and a first medical device over a first ultrasonic communication channel using the ultrasonic transmission component and the ultrasonic receiving component and pairing via a second linking ultrasonic signal and coupling to communicate via a second communication ultrasonic signal between the ultrasonic remote control device and a second medical device over a second ultrasonic communication channel using the ultrasonic transmission component and the ultrasonic receiving component; and
   an interface that displays, at a same time, representations of both the first medical device and the second medical device and enables selection and control of the first medical device independently from selection and control of the second medical device,
   wherein the remote control device controls only one of the first medical device or the second medical device at a time using the ultrasonic communication component.

16. The ultrasonic remote control device of claim 15, wherein one or more of the first medical device and the second medical device is a dialysis machine.

17. The ultrasonic remote control device of claim 15, wherein the ultrasonic transmission component broadcasts the first linking ultrasonic signal or the second linking ultrasonic signal to announce an intent to establish a communication link to a selected one of the first medical device or the second medical device, and wherein the ultrasonic receiving component receives from the selected one of the first medical device or the second medical device an acknowledgement ultrasonic signal to acknowledge the communication link established with the ultrasonic remote control device.

18. The ultrasonic remote control device of claim 17, wherein, after acknowledgment of the communication link, the ultrasonic receiving component receives from the selected one of the first medical device or the second medical device information bursts along a pattern protocol to make the communication link secure.

19. The ultrasonic remote control device of claim 18, wherein the information bursts include one or more of a sequence of ultrasonic pulses that is based on a time of day of transmission or ultrasonic pulses that are synchronized to a pattern unique to the selected one of the first medical device or the second medical device.

20. The ultrasonic remote control device of claim 15, further comprising a wireless communication component that is different from the ultrasonic communication component, wherein the ultrasonic remote control device is wirelessly coupled to a network via the wireless communication component and adapted to distribute information received from one or more of the medical devices to a remote location.

* * * * *